United States Patent [19]
Gunya et al.

[11] Patent Number: 5,401,261
[45] Date of Patent: Mar. 28, 1995

[54] CONTAINMENT VESSELS FOR HANDLING AND DISPOSING OF LIQUID WASTE

[75] Inventors: Robert E. Gunya, Clarion, Pa.; Otto V. Jackson, Orlando, Fla.

[73] Assignee: Milieu Systems Corp., Twinsburg, Ohio

[21] Appl. No.: 906,206

[22] Filed: Jun. 25, 1992

[51] Int. Cl.⁶ .............................................. A61M 1/00
[52] U.S. Cl. .................................... 604/319; 604/321; 27/23.1; 27/24.2
[58] Field of Search ................. 27/23.1, 21.1, 28, 24.2; 5/604, 606, 611; 604/319, 320, 321, 323

[56] References Cited

U.S. PATENT DOCUMENTS

| | | |
|---|---|---|
| 2,598,170 | 5/1952 | Huebotter . |
| 2,971,686 | 2/1961 | Muhlhoff . |
| 3,784,005 | 1/1974 | Mc Vay . |
| 3,923,000 | 12/1975 | Cloyd . |
| 4,420,517 | 12/1983 | Ali . |
| 4,421,510 | 12/1983 | Ahlbeck . |
| 4,449,984 | 5/1984 | Cruz . |
| 4,505,218 | 3/1985 | Fiarman et al. ................. 116/200 |
| 4,559,049 | 12/1985 | Haan . |
| 4,588,088 | 5/1986 | Allen . |
| 4,748,069 | 5/1988 | Cullen . |
| 4,749,600 | 6/1988 | Cullen et al. . |
| 4,826,494 | 5/1989 | Richmond et al. . |
| 4,982,481 | 1/1991 | Deutscher . |
| 5,002,529 | 3/1991 | Cunningham . |
| 5,019,059 | 5/1991 | Goldberg et al. . |
| 5,045,077 | 9/1991 | Blake . |
| 5,092,858 | 3/1992 | Benson et al. . |
| 5,242,434 | 9/1993 | Terry ............................. 604/317 |

FOREIGN PATENT DOCUMENTS 4142089  6/1992  Germany ............................ 604/319

Primary Examiner—Paul Prebilic
Attorney, Agent, or Firm—Renner, Otto, Boisselle & Sklar

[57] ABSTRACT

A containment vessel for liquid waste includes an inlet for introducing liquid waste into the container. Within the container is a gelling substance which when contacted by the liquid waste transforms the liquid waste into a non-pourable gel. A tip indicator indicates if the vessel has been tipped after the vessel has been put into service. Also, an in-service indicator indicates that the vessel has been put into service and that the tip indicator has been released. A full indicator indicates when the contents of the vessel reaches a predetermined level of fullness. A vent for venting the interior of the vessel during filling of the vessel is automatically closed off when the vessel has reached such predetermined level of fullness. The inlet to the vessel may be connected to a drain opening of an embalming table by means of an expandable tube which allows for adjustment of the height of the table. The vessel is supported in place by a cradle having a handle which is vertically adjustable between a raised position for ease of grasping by an operator and a lower position where the handle acts as a table stop preventing downward movement of the table into engagement with the vessel.

6 Claims, 2 Drawing Sheets

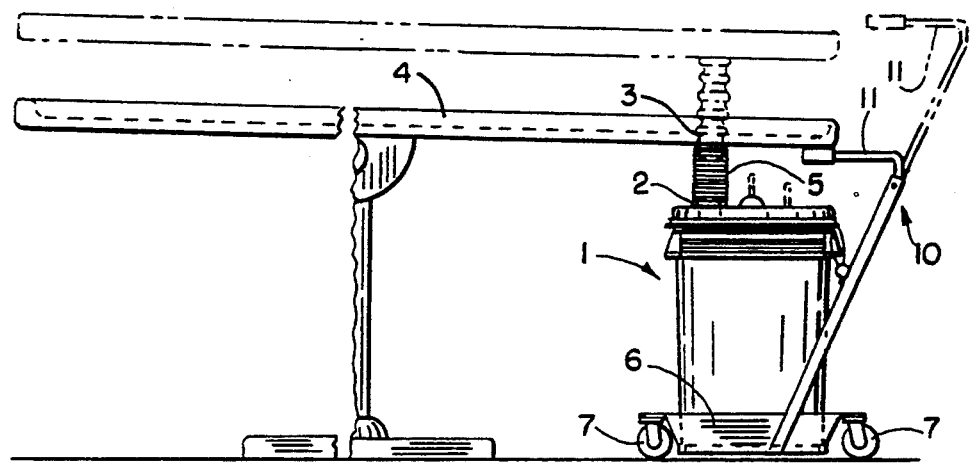
FIG. 1
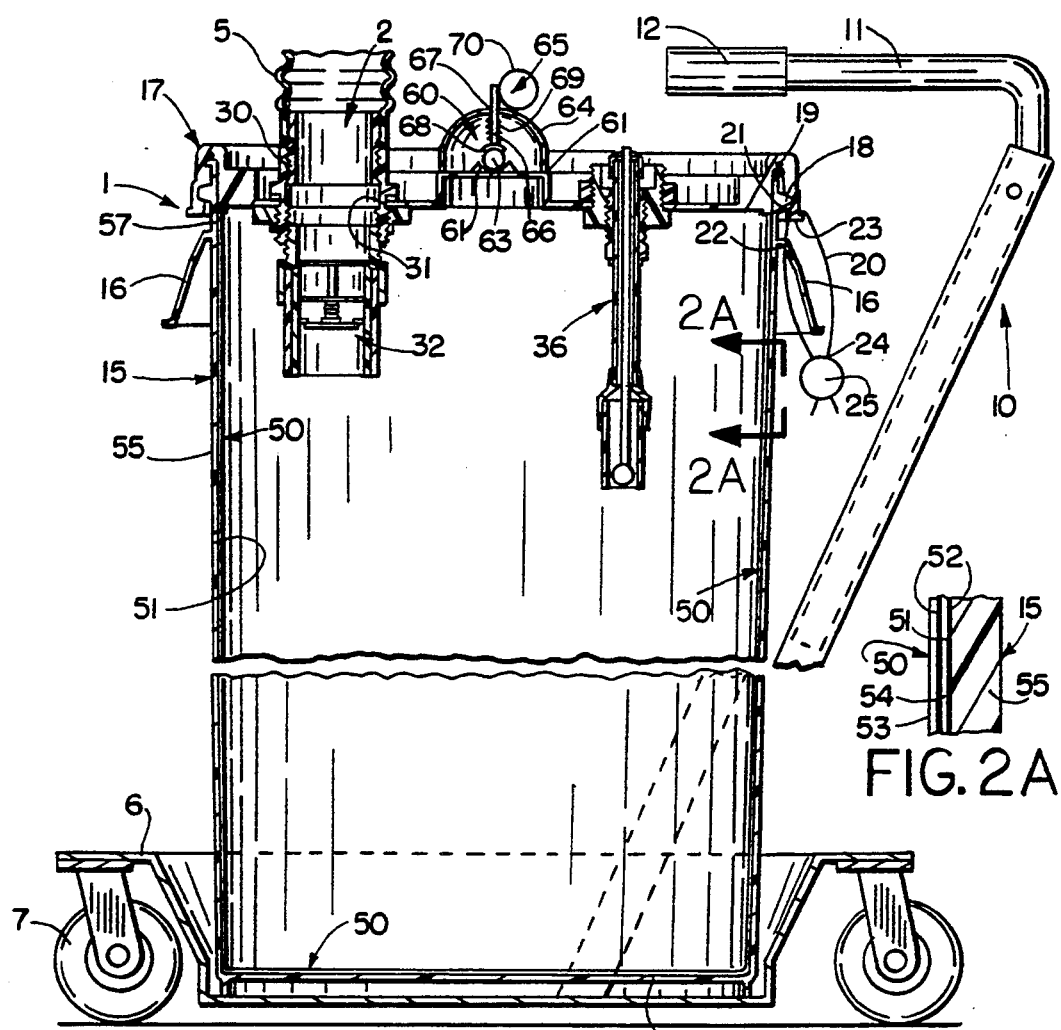
FIG. 2
FIG. 2A

CONTAINMENT VESSELS FOR HANDLING AND DISPOSING OF LIQUID WASTE

FIELD OF THE INVENTION

This invention relates generally to containment vessels for use in the safe handling and disposal of liquid waste products including but not limited to blood and body fluids and embalming fluid from embalming procedures performed by morticians.

BACKGROUND OF THE INVENTION

The manner in which many liquid waste products including blood and body fluids and embalming fluid from embalming procedures performed by morticians is presently being handled and disposed of is of great concern. According to statistics from the Federal Trade Commission (FTC), over two million embalming procedures are performed annually, each producing two and one-half to three and one-half gallons of blood and excess embalming fluid. The Center for Disease Control has stated that contact with these body fluids can potentially transmit infectious diseases such as Human Immunodeficiency Virus (HIV), Acquired Immune Deficiency Syndrome (AIDS), diphtheria, tuberculosis, hepatitis, and so on.

At the present time, virtually all liquid waste from the embalming process is disposed of through conventional sanitary sewers, ending up at sewage treatment plants where it is treated as conventional sewage. The pathogens being released can still potentially transmit infectious diseases. In many cities these effluent pathogens are released into streams, lakes, and rivers, where they reenter the drinking water supply.

SUMMARY OF THE INVENTION

The present invention provides for the safe handling and disposal of liquid waste utilizing holding vessels to capture and contain the liquid waste and convert the liquid waste within the vessels into a non-pourable substance to eliminate any possibility of spillage during transport of the vessels to a location for safe disposal without exposing anyone to the waste materials.

In accordance with one aspect of the invention, one or more layers of a suitable gelling agent are adhered to the interior of the vessels using an adhesive that dissolves when contacted by the liquid waste entering the vessels to release the gelling agent into the liquid waste and thereby transform the liquid waste into a non-pourable substance.

In accordance with another aspect of the invention, when the waste material within the vessels reaches a predetermined level of fullness, an air vent to the interior of the vessels is automatically closed off.

In accordance with another aspect of the invention, the vessels are desirably made of a material having a virtually unlimited life when exposed to the environment, whereby the vessels and their non-pourable contents may be disposed of in conventional landfills where permitted. Also, the vessels and their contents may be incinerated in high temperature incinerating plants.

In accordance with another aspect of the invention, the inlet to each vessel includes a one-way check valve preventing any possibility of spillage or backflow of liquid waste through the inlet.

In accordance with another aspect of the invention, the vessels may be provided with a tip indicator for indicating if the vessels have been tipped after the vessels have been put into service.

In accordance with another aspect of the invention, the vessels may be provided with an in-service indicator to indicate when the vessels have been put into service.

In accordance with another aspect of the invention, the vessels are desirably provided with a full indicator for indicating when the contents of the vessels reach a predetermined level of fullness and for closing off a vent through which air is vented from the interior of the vessels during filling of the vessels through the inlet.

In accordance with another aspect of the invention, a cam lock is desirably provided for drawing a cover into airtight sealing engagement with the container portion of the vessels during attachment of the cover to the container portion. External holes in both the cover and container permit insertion of a wire through the holes and securing the ends of the wires together by a tamper-proof seal after the cover is locked in place.

In accordance with another aspect of the invention, an expandable fill tube is desirably used to connect the inlet to the vessels to a drain opening in an embalming table and the like that permits raising and lowering of the table relative to the vessels without having to disconnect the vessels from the table.

In accordance with another aspect of the invention, a cradle may be used to provide an in-place holding unit for the vessels and a stop preventing downward movement of the embalming table into engagement with the vessels, protecting the vessels against damage. Also, the cradle provides for ease of movement of the vessels from one location to another and eliminates the need for having to lift the vessels when clearing an area.

These and other objects, advantages, features and aspects of the present invention will become apparent as the following description proceeds.

To the accomplishment of the foregoing and related ends, the invention, then, comprises the features hereinafter fully described and particularly pointed out in the claims, the following description and the annexed drawings setting forth in detail a certain illustrative embodiment of the invention, this being indicative, however, of but one of the various ways in which the principles of the invention may be employed.

BRIEF DESCRIPTION OF THE DRAWINGS

In the annexed drawings:

FIG. 1 is a side elevation view of a preferred form of vessel in accordance with this invention, shown supported in place by a cradle beneath an embalming table, with an expandable fill tube extending between the table drain opening and vessel inlet for permitting the table to be raised and lowered relative to the vessel without having to disconnect the vessel from the table;

FIG. 2 is an enlarged fragmentary vertical section through the vessel of FIG. 1 showing the condition of the vessel just prior to placing the vessel into service;

FIG. 2A is a fragmentary enlarged vertical section through a side wall portion of the vessel of FIG. 2 showing two layers of a gelling material adhered to the interior surface thereof;

DETAILED DESCRIPTION OF THE PREFERRED EMBODIMENT

Figure 3:
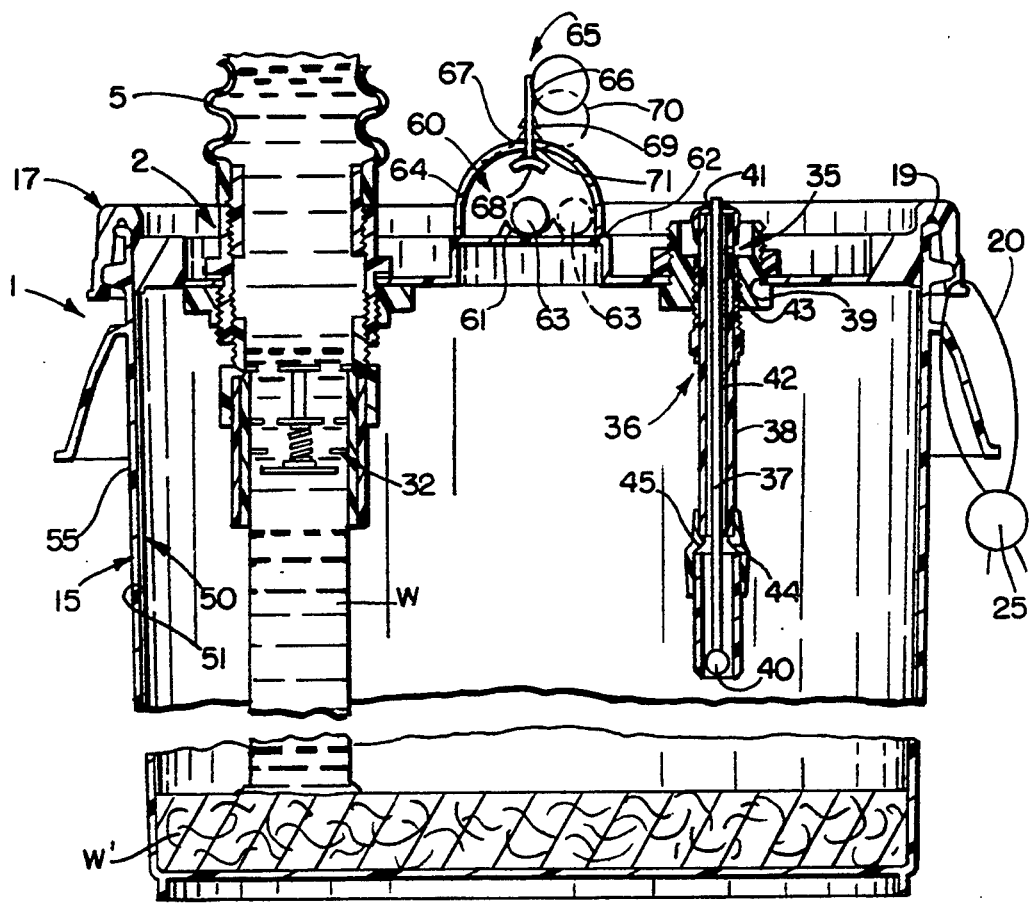
FIG. 3 is a further enlarged fragmentary longitudinal section through the vessel of FIG. 1 showing the vessel after the vessel has been put into service and the vessel has been partially filled with liquid waste material and the liquid waste material has been transformed into a non-pourable gel.

Referring now in detail to the drawings, and initially to FIG. 1, there is shown a preferred form of holding vessel 1 in accordance with this invention for use in the safe handling and disposal of various types of contaminated liquid waste, including but not limited to body fluids and other types of liquid wastes such as chemicals which are waste products in the embalming process. These holding vessels can be used wherever there is a need to collect and dispose of liquid waste materials such as in private embalming rooms, morgues, hospitals, veterinary clinics, medical centers, and various industrial and commercial facilities.

The vessel 1 is shown in FIG. 1 with its inlet 2 connected to the drain opening 3 of an embalming table 4 by means of an expandable corrugated plastic fill tube 5 which automatically expands or contracts to different lengths allowing the table to be raised or lowered as desired.

Preferably, a cradle 6 is provided for supporting the vessel 1 in place off the floor. Swivel and lock type casters 7 on the cradle allow the cradle and thus the vessel supported thereby to be moved about freely from one location to another, thereby eliminating the need for having to lift the vessel when cleaning an area.

The cradle 6 is made of a suitably strong material such as stainless steel. Extending vertically upwardly from the cradle at an angle is a handle 10 including a horizontal handle portion 11 which is vertically adjustable between the raised and lower positions shown in phantom and solid lines, respectively, in FIG. 1. When in the raised position, the handle portion 11 is at a suitable height for ease of grasping by an operator for moving the cradle from one location to another. When in the lower position, the handle portion 11 overlies a portion of the top of the vessel acting as a table stop preventing the table 4 from being lowered into engagement with the vessel and causing damage thereto. Suitable rubber grips 12 may be provided on the ends of the handle for ease in grasping the handle by the operator.

Figure 4:
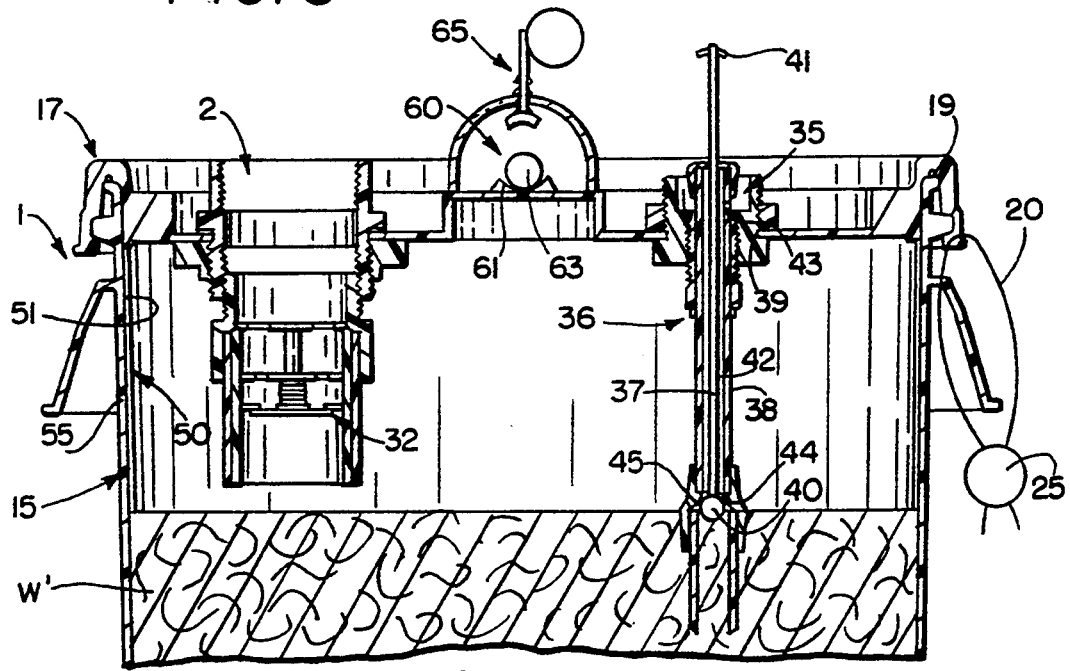
FIG. 4 is an enlarged fragmentary longitudinal section through the vessel, similar to FIG. 3, but showing the vessel filled to a predetermined level of fullness and the air vent to the interior of the vessel closed off.

As seen in FIGS. 2 through 4, the vessel 1 includes an open head container body 15 which is preferably injection molded out of a suitably strong, long lasting plastic such as high density polyethylene, with integral handles 16 on the exterior sides of the container for lifting. Secured to the open top of the container is a screw-on cover 17 which may be made of the same material as the container. Turning the cover a part turn in the tightening direction actuates a cam lock 18 between the cover and container causing the cover to be drawn down against the top of the container compressing an O-ring seal 19 therebetween thus forming an airtight seal around the periphery of the container.

After the cover 17 has been properly secured to the container 15, a wire 20 is preferably inserted through generally vertically aligned holes 21 and 22 in an exterior flange 23 on the cover and in one of the container handles 16 and the ends of the wire attached together as by means of a tamper-proof seal 24 (see FIG. 2) to prevent unauthorized opening of the vessel. Also, an identification tag 25 having a serial number for that particular vessel is desirably attached to the ends of the wire. The serial number is desirably recorded and a permanent record kept to account for the vessel throughout its existence, keeping track of such information as the date of manufacture of the vessel, the date and time the vessel is delivered to a user, the date and time the vessel is picked up from a user, and the date and method of disposal of the vessel.

The inlet 2 to the vessel 1 is formed by suitably attaching a tubular fitting 30 within an opening 31 in the cover 17. Both ends of the fitting 30 are desirably threaded to facilitate attachment of the expandable fill tube 5 to the exterior side of the inlet and a one-way check valve 32 to the interior side of the inlet. The one-way check valve 32 keeps the vessel inlet 2 closed except when liquid waste is entering the vessel thus preventing any possibility of spillage or backflow out through the inlet.

As liquid waste enters the vessel 1 through the inlet 2, the air within the interior of the vessel is vented through an air vent 35. In accordance with the present invention, the air vent 35 is desirably incorporated in the cover 17 as part of a full indicator 36 (see FIGS. 3 and 4) which performs the dual function of indicating when the contents within the vessel have reached a predetermined desired level of fullness and closing off the vent when such desired level of fullness is reached.

In the preferred embodiment disclosed herein, the level indicator 36 comprises an indicator rod 37 axially slidably received within a rod guide 38 suitably mounted within another opening 39 in the vessel cover and extending part way into the interior of the vessel. At the inner end of the indicator rod 37 is a ball float 40 which is forced upwardly by the contents within the container when the contents reach a certain level. However, until that level is reached, the indicator rod 37 is suspended within the rod guide 38 by engagement of a stop 41 adjacent the outer end of the indicator rod against the outer end of the rod guide as schematically shown in FIG. 3.

The vent 35 for venting air from the interior of the vessel 1 during filling of the vessel through the inlet 2 is formed by the clearance space 42 between the indicator rod 37 and rod guide 38 and vent holes 43 and 44 adjacent opposite ends of the rod guide. The outermost vent holes 43 are exterior of the cover, whereas the innermost vent holes 44 are interior of the cover. Adjacent the inner end of the rod guide 38 immediately above the innermost vent holes 44 is a valve seat 45 for a purpose to be subsequently described.

Within the vessel 1 is a suitable gelling material 50 for transforming the liquid waste W inside the vessel into a relatively solid, non-pourable substance W', making it both safer to transport and dispose of without any risk of spillage. In the preferred embodiment disclosed herein, one or more layers of the correct amount of gelling material are adhered to the interior surface 51 of the container using a suitable liquid soluble adhesive 52. FIG. 2a shows two such layers 53 and 54 of gelling material 50 adhesively bonded to the interior surface 51 of the container using a liquid soluble adhesive 52. However, it should be understood that any number of layers of gelling material may be adhesively applied to such interior surface as needed to provide the correct amount of gelling material for gelling the liquid contents. The coating of gelling material initially desirably extends over the entire interior surface of the side wall 55 of the container from the bottom 56 substantially all the way up to the top 57 (see FIG. 2). Also, the bottom interior surface of the container may but need not be initially coated with the gelling material as shown in FIG. 2 if desired.

To coat the interior surface with gelling material, first the interior surface is sprayed with a suitable liquid soluble adhesive 52. Then, before the adhesive dries, the adhesive coating is sprayed or otherwise dusted with a suitable gelling material 50. If more than one layer is desired, the process is repeated until the desired number of layers of gelling material is built up on such interior surface.

Different gelling materials may be used depending on the different types of liquid waste being collected. An example of a gelling material that can be used to gel blood and body fluid and embalming fluid is a 50/50 mixture of starch-g-poly (2-propenamide-CO-2-propenoic acid, potassium salt) and poly (2-propenamide-CO-2-propenoic acid, sodium salt). The mixture is applied to the interior surface in powder form. An example of an adhesive that can be used to adhere the gelling material to the interior surface is a conventional water soluble adhesive.

Coating substantially the entire interior side wall 55 of the container with the gelling material has the advantage that any time any quantity of liquid waste is introduced into the vessel, the liquid waste will be substantially instantaneously converted into a solid waste, thereby virtually eliminating any possibility of spillage. As the content level within the vessel continues to rise, the newly added liquid waste will come into contact with a previously undisturbed portion of the gel coating, thus dissolving the adhesive and releasing additional gelling material into the newly added liquid waste to transform the newly added liquid waste into a non-pourable substance.

The only time this might not happen utilizing the vessel of the present invention is if the vessel is accidentally tipped while liquid waste is being introduced into the vessel and the tipping causes the liquid waste to prematurely dissolve the adhesive and release the gelling material from other parts of the container. To notify the operator of such an occurrence and that the vessel should no longer be used, a tip indicator 60 is desirably provided. As shown in detail in FIG. 3, the tip indicator 60 comprises an outwardly facing socket 61 on the top surface 62 of the cover and a ball 63 loosely received within the socket. A transparent dome 64 provides an enclosure for the ball 63 and socket 61 while permitting viewing of the ball and socket through the dome.

Also, an in-service indicator 65 is desirably provided for preventing the ball 63 from becoming accidentally dislodged from the socket 61 during transporting and storage of the vessel prior to placing the vessel in service and for releasing the ball so that the ball is free to roll out of the socket whenever the vessel is tipped after the vessel has been put into service as an indication that a disproportionate amount of the gelling material has been released into the liquid waste rendering the released gelling material ineffective to transform subsequently introduced liquid waste into a non-pourable gel. The in-service indicator 65 comprises a rod 66 extending axially through an opening 67 in the dome, and a ball holder 68 on the inner end of the rod. When the rod 66 is in its innermost position shown in FIG. 2, the ball holder 68 presses up against the ball 63 thus preventing the ball from becoming accidentally dislodged from the socket 61 before the vessel has been placed in service.

A plurality of flexible barbs 69 along a portion of the length of the rod 66 just beneath the rod opening 67 in the dome 64 provide some resistance to outward movement of the rod from the ball engaging position. However, this resistance can easily be overcome by pulling on a pull ring 70 at the outer end of the rod 66 to pull a portion of the rod and some of the barbs 69 thereon out through the rod hole 67 in the dome 64 to release the ball so the ball is free to roll out of the socket as shown in phantom lines in FIG. 3 whenever the vessel is tipped after the vessel has been put into service. The outward extension of the rod 66 above the dome 64 as shown in FIGS. 3 and 4 provides a visual indication that the vessel has been put into service. The flat end faces 71 on the barbs 69 (see FIG. 3) prevent the in-service indicator rod 66 from being pushed back into the dome once the rod has been pulled out as in FIGS. 3 and 4.

During in-service use of the vessel 1, each time liquid waste is introduced into the vessel through the inlet 2, the content level within the vessel will rise, whereby the newly added liquid waste will always come into contact with a previously undisturbed portion of the gelling material coating 50 and dissolve the adhesive 52 to release the correct amount of gelling material to convert the newly added liquid waste to a solid waste.

FIGS. 3 and 4 show the vessel filled to different levels and the coating of gelling material released up to the level of the liquid waste within the vessel which has been converted to a solid waste W' by the released gelling material. Also, FIG. 4 shows the full indicator rod 37 raised upwardly to its full height indicating that the contents within the vessel have reached a predetermined level of fullness. For example, a desired level of fullness of a vessel having a total capacity of approximately ten and one-half gallons would be approximately eight gallons, leaving an air space of approximately two and one-half gallons above the solid waste within the vessel. Of course, the full indicator rod 37 will start to rise above the top of the vessel as soon as the waste material within the vessel reaches the unsupported level of the float 40 at the inner end of the rod 37, for example, approximately one gallon below the desired maximum level of fullness of vessel. Accordingly, when the full indicator rod 37 first starts to move upwardly, the operator will know that the vessel still has the capacity to receive approximately another gallon of waste material before the full indicator rod reaches its uppermost position. Also, the full indicator rod may be brightly colored, for example, red, making it easily detectable as it starts to rise above the top of the cover. Moreover, the upper end of the rod may have graduations thereon indicating the level of fullness if desired.

When the vessel contents reaches the desired level of fullness as indicated by the full indicator rod 41, the ball float 40 on the lower end of the rod will be forced up into engagement with the valve seat 45, thereby closing off the air vent 35 to the interior of the vessel as schematically shown in FIG. 4. At that time, the operator may remove the fill tube 5 from the vessel inlet 2 of the filled vessel and put into service a new vessel in the same manner as previously described. The filled vessel may then be stored in a safe place until it is picked up and transported to a central location for disposal.

Because the potentially hazardous material within the vessels has been transformed from a liquid state W to a non-pourable gel W', it is classified by the definition of DOT (Department of Transportation) in a much safer category, giving the vessel and its contents a means for the safest possible handling and transportation. In the event of extreme shock or vibration from impact, there is virtually no chance of rupture or leakage from the vessel, due to the fact the contents upon filling becomes an intricate part of the overall resistance to shock and the gelled contents will not pour, substantially reducing the possibility of leakage due to rupture. The entire emphasis is safety in handling and safest means of disposal by eliminating any danger of spillage of the contents during transport. In most cases, the entire vessels and their contents will be incinerated at a high temperature incinerating plant. However, because the vessel contents are considered a solid waste, and the vessels are airtight and made of materials which have a virtually unlimited life when exposed to the environment, the vessels and their contents may also be disposed of in conventional landfills.

Although the invention has been shown and described with respect to a certain preferred embodiment, it is obvious that equivalent alterations and modifications will occur to others skilled in the art upon reading and understanding the specification. The present invention includes all such equivalent alterations and modifications, and is limited only by the scope of the claims.

What is claimed is:

1. A vessel for liquid waste comprising a container having a top and bottom and a side wall extending between said top and bottom, a cover over said top, an inlet for introducing liquid waste into said container, gel means for transforming the liquid waste to a non-pourable gel, means for releasing said gel means into the liquid waste within said container, tip indicator means for indicating if said container has been tipped after the vessel has been put into service, said tip indicator means comprising a ball which is supported in an upwardly facing socket in said cover when said vessel is setting upright, said ball being free to roll out of said socket whenever said vessel is tipped as an indicator that said vessel has been tipped after said vessel has been put into service, and in-service indicator means which when actuated indicates that said vessel has been put into service and releases said ball so that said ball is free to roll out of said socket whenever said vessel is tipped, said in-service indicator means comprising a rod extending through an opening in a transparent dome enclosing said ball and said socket, and a ball holder on an inner end of said rod, said rod being axially movable between a first position in which said ball holder engages said ball for retaining said ball in said socket and a second position out of engagement with said ball for permitting said ball to roll out of said socket whenever said vessel is tipped.

2. The vessel of claim 1 further comprising flexible barb means along a portion of the length of said rod for resisting outward movement of said rod from said first position to said second position, and for preventing inward movement of said rod to said first position once said rod has been moved to said second position.

3. The vessel of claim 1 wherein said tip indicator means indicates if said container has been tipped after the vessel has been put into service as an indication that a disproportionate amount of said gel means has been released into the liquid waste rendering the released gel means ineffective to transform subsequently introduced liquid waste into a non-pourable gel.

4. The vessel of claim 1 further comprising full indicator means for indicating when said container reaches a predetermined level of fullness, said full indicator means comprising a second rod extending axially through an opening in said cover into the interior of said container, a float on an inner end of said second rod which forces said second rod outwardly a predetermined amount relative to said cover when said container reaches such predetermined level of fullness, a rod guide for said second rod, said rod guide having a seat, and said float including a second ball which is moved axially outwardly into engagement with said seat when said container reaches said predetermined level of fullness.

5. The vessel of claim 4 wherein said full indicator means includes a vent between said second rod and said rod guide for venting air from the interior of said container during filling of said container with liquid waste through said inlet, said vent being closed off by said second ball when said second ball engages said seat.

6. The vessel of claim 1 wherein said inlet contains a check valve permitting one-way flow of the liquid waste through said inlet into said container.

* * * * *